United States Patent [19]

Larkin et al.

[11] 4,434,309

[45] Feb. 28, 1984

[54] OLIGOMERIZATION OF PREDOMINANTLY LOW MOLECULAR WEIGHT OLEFINS OVER BORON TRIFLUORIDE IN THE PRESENCE OF A PROTONIC PROMOTER

[75] Inventors: John M. Larkin; Walter H. Brader, Jr., both of Austin, Tex.

[73] Assignee: Texaco Inc., White Plains, N.Y.

[21] Appl. No.: 389,737

[22] Filed: Jun. 18, 1982

[51] Int. Cl.[3] ............................ C07C 1/16; C07C 5/00
[52] U.S. Cl. ...................................... 585/10; 585/18; 585/254; 585/255; 585/525
[58] Field of Search ................... 585/10, 12, 18, 255, 585/510, 512, 520, 522, 525, 526, 532, 642, 648, 660, 664, 254

[56] References Cited

U.S. PATENT DOCUMENTS 4,172,855 10/1979 Shubkin et al. ...................... 585/255
4,225,739 9/1980 Nipe et al. ............................ 585/525

*Primary Examiner*—Curtis R. Davis
*Attorney, Agent, or Firm*—Jack H. Park; Kenneth R. Priem; David L. Mossman

[57] ABSTRACT

A mixture of predominantly low molecular weight alpha olefins may be oligomerized over a boron trifluoride catalyst and a protonic promoter. When the oligomers are hydrogenated they provide a synthetic lubricant base stock having excellent properties. The alpha olefins may be derived from ethylene polymerization or wax pyrolysis. An inert organic solvent may be present. Preferably, the olefin mixture is made up of greater than 50 weight weight percent of at least one low molecular weight alpha olefin having 4 to 6 carbon atoms and less than 50 weight percent of at least one higher molecular weight alpha olefin having 8 to 18 carbon atoms.

20 Claims, No Drawings

OLIGOMERIZATION OF PREDOMINANTLY LOW MOLECULAR WEIGHT OLEFINS OVER BORON TRIFLUORIDE IN THE PRESENCE OF A PROTONIC PROMOTER

BACKGROUND OF THE INVENTION

1. Field of the Invention

The invention relates to methods of oligomerizing olefins over a boron trifluoride catalyst together with a promoter, and more particularly relates to methods of oligomerizing a mixture of predominantly low molecular weight alpha olefins over a boron trifluoride catalyst in the presence of an organic protonic promoter.

2. Description of Related Methods

Nearly all of the patents issued on olefin oligomerization have involved alpha olefins. For example, see U.S. Pat. No. 3,410,925 to Eby, et al. in which alpha olefins are mixed with alkylatable aromatic hydrocarbons over a Friedel-Crafts catalyst to form an alkylation sludge which is then mixed with olefins having 3 to 18 carbon atoms which are also passed over the catalyst to produce olefin dimers. U.S. Pat. No. 3,652,706 to Saines, et al. describes the polymerization of alpha olefins having 2 to 20 carbon atoms over a Friedel-Crafts metal halide catalyst plus a hydrogen form of mordenite to produce compounds having a molecular weight between 700 and 2,500. Production of a gasoline fuel composition is described in U.S. Pat. No. 3,749,560 to Perilstein which occurs by reacting a mixture of mono olefins over a Friedel-Crafts catalyst heated to a temperature around 145° C. to produce oligomers having molecular weights between 350 to 1,500. Also, U.S. Pat. No. 3,149,178 to Hamilton, et al. reveals an improved method for making polymerized olefin synthetic lubricants via a particular distillation technique of oligomers made from alpha mono olefins using a Friedel-Crafts catalyst. Alpha olefins having six to twelve carbon atoms may be dimerized in the presence of a Friedel-Crafts catalyst according to the method described in U.S. Pat. No. 4,172,855 to Shubkin, et al.

It is also known that the term "Friedel-Crafts catalysts" includes boron trifluoride among other metal halide-type Lewis catalysts, see *Kirk-Othmer Encyclopedia of Chemical Technology*, Third Edition, Vol. 11, pg 292. Boron trifluoride has also been known to polymerize olefins, as seen in F. Albert Cotton, et al., *Advanced Inorganic Chemistry: A Comprehensive Text*, Interscience Publishers, 1962, p. 191.

A number of patents have also used $BF_3$ to oligomerize olefins. For example, British Pat. No. 1,323,353 describes the use of wax cracked alpha olefins as precursors for synlube fluids. U.S. Pat. No. 2,780,664 to Serniuk describes the reaction of conjugated dienes with mono olefins over $BF_3$ promoted by an ether mixed with a halo alkane diluent at a temperature from −30° to 100° C. to produce oligomers suitable for drying oils. Alpha olefins having from 5 to 20 carbon atoms are oligomerized using $BF_3$ plus an alcohol or water promoter as described in U.S. Pat. No. 3,382,291 to Brennan. In this patent, $BF_3$ and a mixture of $BF_3$ plus the promoter complex are introduced in two separate streams. Another U.S. Pat. No. by Brennan, 3,742,082, concerns the dimerization of alpha olefins via $BF_3$ which is promoted with phosphoric acid or water at a temperature from 100° to 150° C. U.S. Pat. No. 3,763,244 to Shubkin, describes the oligomerization of n-alpha olefins having 6 to 16 carbon atoms over $BF_3$ promoted with water, at a temperature between 10° and 60° C. where it is preferred that $BF_3$ is added continuously.

Yet another U.S. Pat. No. to Brennan, 3,769,363 describes the oligomerization of olefins having 6 to 12 carbon atoms using $BF_3$ with a carboxylic acid promoter having at least 3 carbon atoms at a temperature between 0° and 20° C. to produce olefins heavy in trimer form. U.S. Pat. No. 3,780,128 also to Shubkin relates to the oligomerization of alpha olefins having 6 to 16 carbon atoms in which $BF_3$ is employed in a molar excess of alcohol. U.S. Pat. No. 3,876,720 to Heilman, et al. describes a two-step procedure by which alpha olefins having 8 to 12 carbon atoms are converted to vinylidene olefins which are then reacted over a 1:1 molar complex of $BF_3$ and alcohol to produce oligomerized vinylidene olefins. A method for oligomerizing both short and long chain alpha olefins having from 14 to 20 carbon atoms simultaneously over $BF_3$ with an alcohol or water promoter at 0° to 60° C. with a monomer recycle is described in U.S. Pat. No. 4,225,739 to Nipe, et al. There is also U.S. Pat. No. 4,263,465 to Sheng, et al. which describes a two-step process for reacting 1-butene with a higher alpha olefin over $BF_3$ in the presence of a proton donor at a temperature from −30° to 50° C. to produce an oligomer having 8 to 18 carbon atoms. The intermediate oligomer is reacted with other higher alpha mono olefins over the same catalyst system from −30° to 60° C. to produce oligomers having 20 to 40 carbon atoms. For more information on $BF_3$-catalyzed oligomerization of alpha olefins, see Brennan, "Wide-Temperature Range Synthetic Hydrocarbon Fluids," Ind. Eng. Chem. Prod. Res. Dev. 1980, Vol. 19, pp 2–6 and Shubkin, et al., "Olefin Oligomer Synthetic Lubricants: Structure and Mechanism of Formation," Ind. Eng. Chem. Prod. Res. Dev. 1980, Vol. 19, pp 15–19.

U.S. Pat. No. 4,213,001 reveals a method of homopolymerizing an alpha olefin by utilizing boron trifluoride under pressure in the presence of a suspended particulate absorbent material. The absorbent material may be silica, alumina, magnesia, zirconia, activated carbon, the zeolites, silicon carbon, silicon nitride, titania, thoria, porous polyvinyl alcohol beads, porous polyethylene glycol beads and the like.

Additional methods in this field include that of U.S. Pat. No. 4,045,507 which involves a multi-stage, continuous process for polymerizing alpha olefins having 5 to 14 carbon atoms in the presence of boron trifluoride and a co-catalyst. A process involving the copolymerization of propylene or propylene plus higher alpha olefins with small amounts of ethylene in the presence of a vanadium-containing catalyst, an aluminum-containing catalyst and a Friedel-Crafts catalyst is described in U.S. Pat. No. 4,182,922 and may be of particular interest. U.S. Pat. No. 4,263,465 involves the preparation of a low viscosity synthetic lubricant by polymerizing 1-butene to an oligomer containing a number average of about 8 to 18 carbon atoms and copolymerizing the oligomer with an alpha-mono olefin having 8 to 18 carbon atoms to produce a copolymer having an average of about 20 to 40 carbon atoms.

U.S. Pat. No. 4,300,006 issued on Nov. 10, 1981. It describes a process for producing a hydrocarbon oil by contacting a mixture of alpha and at least 50 weight percent internal olefins with a boron trifluoride dimerization catalyst. However, the productivity of useful products from the process revealed in U.S. Pat. No. 4,300,006 is quite low. For example, an alkane diluent is found to be necessary in the process described therein. When the lights and heavies are distilled out as required by the method, little useful product results. Further, this method requires a much longer reaction time and a higher catalyst concentration than desired. It would be beneficial if a method for producing synthetic lubricants could be devised which would overcome the aforementioned disadvantages.

Also of interest is U.S. Pat. No. 4,214,112. It discloses a process for producing an olefin oligomer which involves polymerizing olefins having not less than 6 carbon atoms in the presence of a specified catalyst system. The system consists of an aluminum halide, a polyhydric alcohol derivative and a nickel compound or a cobalt compound. The nickel and cobalt compounds are listed as nickel monoxide, trinickel tetroxide, nickel sequioxide, nickel hydroxide, nickel sulfide, nickel sulfate, nickel acetate, nickel oleate, nickel stearate, nickel diatomaceous earth, nickel chloride, nickel acetylacetonate, nickel peroxide, cobalt carbonate, dicobalt octacarbonyl, cobalt chloride, cobalt nitrate, cobalt oxide, cobalt hydroxide, cobalt sulfide, cobalt sulfate, cobalt acetate, cobalt oleate, cobalt acetylacetonate, etc. and combinations thereof. The compounds used in the examples therein are nickel oxide, nickel chloride, nickel oleate, nickel carbonate and cobalt chloride.

In the field of oligomerizing olefins for synthetic lubricants, it is a continual problem to produce olefins having low viscosities at room temperature and below but which have a high viscosity index and low volatility.

SUMMARY OF THE INVENTION

The invention concerns a process for oligomerizing mono olefins comprising contacting a mixture of alpha mono olefins which consists essentially of greater than 50 weight percent of at least one low molecular weight alpha olefin having 4 to 6 carbon atoms and less than 50 weight percent of at least one higher molecular weight alpha olefin having 8 to 18 carbon atoms, with a catalyst comprising boron trifluoride in the presence of an organic protonic promoter selected from the group consisting of alcohols and carboxylic acids.

DESCRIPTION OF THE PREFERRED EMBODIMENTS

It has been surprisingly discovered that oligomers which have an unusual blend of properties may be made by reacting predominantly low molecular weight alpha mono olefins over a boron trifluoride catalyst and an organic, protonic promoter. No other researchers have accomplished this objective in this way.

The olefin feedstock may be generally expressed as a mixture of alpha olefins having the formula

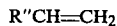

where R″ is an alkyl radical of 2 to 4 carbon atoms for the low molecular weight olefins and 6 to 16 carbon atoms for the higher molecular weight alpha olefins. It is especially preferred that the two sizes of olefins be used together; namely, at least one alpha olefin having 4 to 6 carbon atoms (1-butene, 1-pentene and 1-hexene) and at least one higher molecular weight alpha olefin having 8 to 18 carbon atoms. This combination of low and high molecular weight olefins helps contribute to the unique properties of the resulting oligomers. However, it is also preferred that the majority of the olefin reactant mixture be the low molecular weight alpha-olefins. An especially preferred low molecular weight alpha olefin is 1-butene.

The higher alpha olefins to be oligomerized in this invention may be obtained by a multi-step process. In the first step, ethylene is transformed into linear alpha olefins using Ziegler technology as disclosed in various patents, including U.S. Pat. Nos. 3,424,815; 3,482,000; 3,424,816; 3,444,264; 3,444,263; 3,502,741; 3,510,539; 3,478,124; and 3,441,631. These patents are incorporated herein by reference. The result of this conversion of ethylene is a mixture of alpha olefins ranging from C-4 to above C-24. The alpha olefins ranging from about C-4 or C-8 to C-18 or any other range of alpha olefins desired within C-4 to C-24 are separated and oligomerized using boron trifluoride and the promoter of this invention. The alpha olefins of below about 8 and above about 18 carbon atoms are combined and subjected to an isomerization/disproportionation process described in the literature, for example: U.S. Pat. No. 3,647,906; 3,728,414 and 3,726,938, which are incorporated herein by reference.

The olefins resulting from this isomerization/disproportionation process are a mixture of alpha and internal olefins of various molecular weights. The olefins should have a total number of carbon atoms in the range from about 8 to 18 or any selected cut within that range may be oligomerized with boron trifluoride and a protonic promoter. Those olefins may be mixed with the alpha olefins from the initial ethylene made feed and oligomerized.

Such a process provides a systematic way to control which olefin cut is selected for oligomerization, and also uses the discarded cuts for additional feed. Olefins useful in the method of this invention may also be produced by wax pyrolysis.

Generally, the weight ratio of the low molecular weight alpha olefins (C$_4$–C$_6$) to the higher molecular weight alpha olefins is preferred to range from greater than 1:1 to 3:1.

The catalyst of choice is boron trifluoride. However, it is well known that boron trifluoride by itself is not very effective and promoters (sometimes called cocatalysts) must be employed to activate the boron trifluoride. The most effective promoters for the method of this invention are the organic, protonic promoters of alcohols and carboxylic acids, which are known in the art. When alcohols and carboxylic acids are mentioned in the previous methods as being suitable promoters, water is usually also mentioned as being useful. However, as will be shown, water surprisingly does not serve as an effective promoter in the method of this invention. The preferred organic, protonic promoter for this invention is 1-butanol.

It is preferred that the boron trifluoride catalyst be present in an amount of from 0.75 to 3.0 weight percent, based on the olefin mixture amount. On the other hand, the organic, protonic promoter should be present in an amount such that the molar ratio of promoter to olefin mixture is from 0.005 to 0.2.

One skilled in the art may find an inert, organic solvent, such as cyclohexane, useful in conducting the oligomerization. However, the amount of solvent should be less than about 50 weight percent based on the olefin mixture. The temperature range at which the oligomerization may be performed successfully is between 25° and 75° C., with a preferred range between 30° to 120° C. The pressure range of the reaction may run from zero to 1,000 psig although autogenous pressures are preferred. The pressure should be sufficient to maintain a liquid phase reaction. The oligomerization of the olefins may be conducted in a batch or continuous mode.

In order to form materials which have adequate oxidate stability for lubricants, the oligomerized olefins are optionally hydrogenated either partially or totally. This hydrogenation is done by procedures known to those skilled in the art as exemplified by U.S. Pat. Nos. 4,045,508; 4,013,736; 3,997,622 and 3,997,621. A particularly preferred catalyst for this hydrogenation is a nickel-copper-chromium oxide catalyst described in U.S. Pat. No. 3,152,998, incorporated herein by reference. A cobalt-copper-chromium oxide catalyst would also be useful.

Kinematic viscosities at the standard temperature of 210° F. are given in centistokes. The viscosity index (VI) is the change in viscosity with temperature such that the higher the number, the lower is the change in viscosity with temperature. Conversely, a low VI signifies a large change in viscosity with temperature. Pour point is a measure of the temperature, in degrees Centigrade, at which the sample will begin to pour. Below that temperature the composition may generally be regarded as a solid. Thermogravimetric analysis (TGA) is a test which measures volatility by measuring the weight percent of sample remaining at various temperatures as the temperature is raised in a slow, uniform manner. When a sample's TGA indicates that at least 80% remains at 233° C., the sample is considered sufficiently non-volatile to be useful in lube oil formulations.

Synthetic lubricant components which are expected to be used as lubricants should contain olefin oligomers having about twenty carbon atoms and greater. Thus, the only preferred separation step is to remove all olefin oligomers having less than about twenty carbon atoms. These lower carbon number oligomers may be removed before or after the hydrogenation step.

The process of this invention is further illustrated by the following examples.

EXAMPLE 1

Hexene-1 Oligomerization with BF$_3$/Propionic Acid

Boron trifluoride was introduced as a gas into 53.2 g of hexene-1 maintained at 13° C. until the solution was saturated. Saturation was maintained by continuous introduction of BF$_3$, as a solution of 5.0 g propionic acid in 150 ml hexene-1 was added simultaneously over a 2.85 hr period. Ice water cooling was used to moderate the exothermic heat and keep the temperature near 13° C. After 2 hours more at 10°–14° C. in the presence of BF$_3$, the solution was flushed with nitrogen and 120 ml of water was added. The mixture was stirred for 1 hour and the water withdrawn. The top layer was washed with 2×120 ml portions of water, dried over anhydrous sodium sulfate, and stripped at 17 mm Hg on a rotary evaporator at 93° C. Yield of hexene oligomer was 97.8%; its analysis by liquid chromatography is indicated in Table 1.

EXAMPLES 2–9

Hexene-1 Oligomerization with BF$_3$ and Various Promoters

The procedure of Example 1 was essentially repeated except that other promoters, and in some cases other conditions were used. The results are tabulated in Table I. It is apparent that high yields of oligomers consisting of tetramers and higher polymers can be obtained, and that the alcohol promoters give the best results.

TABLE I

1-HEXENE OLIGOMERIZATION WITH BF$_3$

| Ex. | Promoter | Moles Promoter/ Mole Olefin | Temp. °C. | Add'n Mode[a] | Yield % | Oligomer distribution, % |  |  |  |  |  |  |
|---|---|---|---|---|---|---|---|---|---|---|---|---|
|  |  |  |  |  |  | dimer | trimer | tetramer | pentamer | hexamer | heptamer | higher |
| 1 | C—C—CO$_2$H | 0.0280 | 13 | A | 97.8 | 4.6 | 17.5 | 44.0 | 14.9 | 11.9 | 5.1 | — |
| 2 | 1-butanol | 0.277 | 13 | A | 97.8 | — | 0.5 | 1.6 | 10.2 | 26.0 | 27.5 | 34.3 |
| 3 | 1-propanol | ~0.2 | 20–100+ | C | N.D. | 5.3 | 24.0 | 32.8 | 23.5 | 9.1 | 2.9 | 0.9 |
| 4 | 1-butanol | 0.0267 | 14 | B | 93.3 | — | — | 3.7 | 20.9 | 27.1 | 23.4 | 24.7 |
| 5 | 1-butanol | 0.0271 | 27 | B | 92.1 | — | 0.5 | 6.0 | 27.6 | 31.7 | 20.7 | 13.5 |
| 6 | DBPC[b] | 0.0234 | 22 | B | 26 | 27.8 | 60.5 | 9.7 | 2.1 | — | — | — |
| 7 | DGA ®[c] | 0.0211 | 14 | B | 4.6 | 36.4 | 36.3 | 16.5 | 7.2 | 2.3 | 0.6 |  |
| 8 | Softanol ® A (C$_{12}$-C$_{14}$ sec alkanols) | 0.117 | 28→80+ | B | 84.8 | 18.2 | 50.6 50.5[d] | 23.4 31.2 | 7.8 8.2 | 4.1 | 1.0 | 1.0 |
| 9 | di n-butylamine | 0.132 | 14→39 | B | ~0 | — | — | — | — | — | — | — |

[a]Modes of addition: A = promoter and olefin added to BF$_3$, B = olefin added to promoter and BF$_3$, C = BF$_3$ added to promoter and olefin.
[b]DBPC = di-t-butyl-p-cresol.
[c]DIGLYCOLAMINE brand of 2-(2-aminoethoxy)ethanol.
[d]Analysis on a dimer-free basis.
[e]N.D. = not determined.

EXAMPLE 10

Oligomerization of a C$_4$/C$_6$/C/C$_{10}$ Alpha Olefin Mixture

An olefin mixture (1000 g) consisting of butene-1/hexene-1/octene-1/decene-1 in a respective weight ratio of 3.6/1/1/1 was added over a 3.5 hour period to a stirred mixture of 430 g cyclohexane, 23.0 g 1-butanol, and 37 g BF$_3$ maintained near 24° C. in a 1-gallon pressure vessel. After stirring for 1.5 hours more, 300 ml water was added, and stirring was continued for one-half hour more. The water layer was separated, the organic layer washed with 4×500 ml of water, dried over anhydrous sodium sulfate, and stripped on an evaporator at 31 mm Hg and 92° C. A quantitative yield of colorless liquid having an average carbon number of 36.6 (weight average) remained; only 7% of the material was less than C$_{20}$. The pour point was −45° F., the 210° F. kinematic viscosity was 5.06 cS, and the viscosity index was 99; thermogravimetric analysis (+10° C./min) indicated 87% of the material remained at 233° C. These properties are like those desired for a lubricating oil (for example, in an automobile crankcase).

A portion of the material was hydrogenated at 210° C./2000 psig $H_2$ over the nickel-copper-chromium oxide catalyst of U.S. Pat. No. 3,152,998 and vacuum stripped at 0.55 mm Hg (116° head temp.); 1% of the material was removed overhead. The colorless bottoms product had a 210° F. kin. vis. of 5.8 cS, a VI of 100, pour point of -45F, and 78.3% remained in TGA at 233° C. when the temperature was raised at +10° C./min.

EXAMPLES 11-17

3.6/1/1/1 Weight Ratio $C_4C_6/C_8/C_{10}$ Alpha Olefins Under Various Conditions The procedure of Example 10 was essentially repeated except for differences as noted in Table II. The conditions and results are listed in Table II; products which contained more than 40% oligomers lighter than $C_{20}$ were not hydrogenated. It can be noted that alcohols, and in particular 1-butanol, are promoters, that temperature in the range 23°-49° C. is not critical, and that the concentration of $BF_3$ should be greater than 0.32%. It can be further noted that the hydrogenated products have excellent properties for synthetic lubricants.

be noted that: (1) excellent synthetic lubricants can be obtained; (2) the effective concentration of $BF_3$ should be greater than 0.62 wt.% in order to obtain oligomers of the correct molecular weight range with these 1-butene mixtures; and (3) water doesn't serve as an effective promoter.

TABLE III

OLIGOMERIZATION OF VARIOUS ALPHA OLEFIN MIXTURES

| Ex. | Olefin Mix[a] | Promoter | wt % $BF_3$ | Temp. °C. | Addition Time Hrs. | Holding Time Hours | C# avg. | Avg. Mol wt. wt. avg. | % Below $C_{20}$ | kin Vis 210° F., cS | VI | Pour Pt. °F. | TGA % left at 233° C. |
|---|---|---|---|---|---|---|---|---|---|---|---|---|---|
| 18 | A | 1-butanol | 1.36 | 37 | 2 | 1.5 | 24.1 | 26.2 | 32 | 4.88 | 93 | <−50 | 77 |
| 19 | B | 1-butanol | 0.62 | 36 | 2 | 1.5 | 17.9 | 19.2 | 75 | | | | |
| 20 | C[b] | 1-butanol | 1.62 | 35 | 2 | 2.25 | 26.0 | 28.6 | 25 | 4.93 | 102 | −55 | 86 |
| 21 | B | $H_2O$ | 1.15 | 38 | 2 | 1.5 | 20.2 | 22.0 | 65 | | | | |
| 22 | B | 1-butanol | 1.7 | 39 | 2 | 1.5 | 23.8 | 26.7 | 22 | 5.05 | 115 | −30 | 88 |
| 23 | C[b] | 1-butanol | 1.68 | 32 | 2 | 2 | 20.7 | 22.3 | 50 | 4.09 | 93 | −55 | 87 |
| 24 | D[b] | 1-butanol | 1.68 | 32 | 2 | 2 | 28.7 | 31.5 | 15 | 5.68 | 105 | −35 | 92 |
| 25 | B | 1-butanol | 1.1 | 39 | 2 | 1.5 | 23.3 | 26.0 | 45 | 5.20 | 118 | −25 | 87 |

[a]The olefin mixtures are defined as follows:
A = 4/1/1/1 wt. ratio $C_4/C_6/C_8/C_{14}$ α-olefins
B = 4/1/1/1 wt. ratio $C_4/C_6/C_{14}/C_{16}$ α-olefins
C = 4/1/1 wt. ratio $C_4/C_{10}/C_{14}$ α-olefins
D = 1.65/1 wt. ratio $C_4/C_{14}$ α-olefins
[b]The promoter was present in the olefin mix rather than in the solvent.

EXAMPLES 18-25

$BF_3$ Catalyzed Oligomerizations of Various Mixtures

The procedure of Example 10 was essentially repeated with various other olefin mixtures as listed in Table III. All mixtures contain butene-1 as the largest single component. For those olefin mixes labeled "C" and "D", the 1-butanol was added with the olefin. It can

EXAMPLE 26

Oligomerization of butene-1/tetradecene-1 without Solvent

To a 1410 ml rocking autoclave containing 14 g of $BF_3$ there was added 791.6 g of a 1.65/1 weight ratio $C_4/C_{14}$ alpha olefin mixture and 8.4 g 1-butanol over a 4¾ hour period with the clave contents at about 45° C. average temperature. After 2 hours more rocking (interrupted by standing without agitation for 16 hours), 100 ml of water was added, and rocking was terminated after one-half hour. The water layer was withdrawn and the top layer washed with 4×400 ml water followed by stripping at 94° C. and 33 mm Hg. The remaining product (755 g) had a weight average carbon number of 40. This experiment indicates that oligomerization without solvent yields a higher molecular weight product.

EXAMPLE 27

Oligomerization of Butene-1/Decene-1/Tetradecene-1 without Solvent

The procedure of Example 26 was essentially repeated except the olefin mix consisted of a 4/1/1 weight

TABLE II

OLIGOMERIZATION OF A $C_4/C_6/C_8/C_{10}$ ALPHA OLEFIN MIXTURE

| Ex. | Promoter | Moles Promoter/ Moles Olefin | wt. %* $BF_3$ | Temp. °C. | Addition Time Hrs. | Holding Time Hours | C# avg. | Avg. Mol wt. wt. avg. | % Below $C_{20}$ | kin Vis 210° F., cS | VI | Pour Pt. °F. | TGA % left at 233° C. |
|---|---|---|---|---|---|---|---|---|---|---|---|---|---|
| 11 | 1-butanol | 0.022 | 2.95 | 48 | 1.1 | 1.5 | 27.5 | 31.2 | 18 | 4.75 | 89 | −55 | 76 |
| 12 | 1-butanol | 0.007 | 1.36 | 49 | 1.5 | 1.0 | 23.0 | 24.7 | 23 | 3.47 | 73 | <−50 | 64 |
| 13 | Propionic acid | 0.007 | 1.24 | 48 | 1.5 | 1.0 | 13.1 | 12.8 | 100 | — | — | — | — |
| 14 | $C_{12}$-$C_{14}$ Sec alcohols | 0.007 | 1.28 | 48 | 1.5 | 1.5 | 21.0 | 23.4 | 40 | 3.09 | 65 | <−50 | 41 |
| 15 | 1-butanol | 0.007 | 1.52 | 23 | 3.75 | 1.5 | 34.5 | 36.0 | 4 | 4.80 | 90 | −60 | 67 |
| 16 | 1-octanol | 0.007 | 1.36 | 47 | 2 | 2.5 | 19.2 | 20.6 | 70 | — | — | — | — |
| 17 | 1-butanol | 0.0019 | 0.32 | 38 | 2.7 | 1.5 | 16.6 | 16.8 | 95 | — | — | — | — |

*Based on wt. of olefin mixture ratio $C_4/C_{10}C_{14}$ alpha olefins, only 4.4 g 1-butanol was added, only 8 g of $BF_3$ was used, and the overnight standing was not conducted. The oligomeric product had a weight average carbon number of 27.0.

EXAMPLE 28

Oligomerization of $C_4/C_{10}/C_{14}$ Alpha Olefin Mix

The olefin mix of Example 27 was reacted essentially according to the procedure of Example 10 except that the amount of olefin mix was only 550 g, the amount of $BF_3$ was 9.0 g (1.6 wt.%) and the amount of promoter was 6.0 g 1-butanol. The solvent cyclohexane amounted to 1600 g rather than 430 g. After work-up similar to Example 10, the product obtained has a weight average carbon number of 13.5. This example illustrates the inadvisability of using large quantities of solvent.

EXAMPLE 29

Continuous Oligomerization of a $C_4/C_{14}$ Alpha Olefin Mixture

A liquid feed consisting of 25.92 lbs 1-butene, 15.68 lbs. 1-tetradecene and 180 g 1-butanol was pumped at 624 g/hr. to a reactor system consisting of a 500 ml stirred reactor connected in series to a 500 ml tubular reactor in vertical configuration. Liquid entered near the bottom of the stirred reactor, exited near the top, and entered the tubular reactor at the bottom while exiting at the top. The reactor pressure was maintained at 122–130 psig by means of a back-pressure regulator, and the effluent line exit was immersed in water. Boron trifluoride was metered to the stirred reactor in a separate line at an average rate of 7.6 g/hr. (1.2% weight concentration based on olefin). The stirred and tubular reactor were approximately 35° C. each.

After removal of water, and additional washing of the effluent with water, followed by vacuum stripping, the product oligomer was obtained in 90.2% yield. It has an average carbon number of 28.7.

When the reactor was operated as above except that the average liquid feed rate was 448 g/hr. and average $BF_3$ concentration was 1.5 wt.%, the product oligomer, obtained in 100% yield, had an average carbon number of 39.0.

Many modifications may be made in the method of this invention without departing from its scope which is defined only by the appended claims. For example, it would be expected that one skilled in the art could change the $BF_3$ promoter, the temperature, the pressure or the modes of addition from those actually employed herein in trying to maximize the conversion or to change the oligomer properties.

We claim:

1. A process for oligomerizing mono olefins comprising contacting a mixture of alpha mono olefins which consists essentially of greater than 50 weight percent of at least one low molecular weight alpha olefin which is 1-butene and less than 50 weight percent of at least one higher molecular weight alpha olefin having 8 to 18 carbon atoms, with a catalyst comprising boron trifluoride in the presence of an organic, protonic promoter selected from the group consisting of alcohols and carboxylic acids at a temperature in the range of about 25° to 75° C. and a pressure that is sufficient to maintain a liquid phase reaction.

2. The process of claim 1 in which the catalyst is present in an amount of from 0.75 to 3.0 weight percent, based on the olefin mixture.

3. The process of claim 1 in which the molar ratio of organic, protonic promoter to olefin mixture is from 0.005 to 0.2.

4. The process of claim 1 in which the organic, protonic promoter is 1-butanol.

5. The process of claim 1 in which less than 50 weight percent of an inert organic solvent is employed, based on the olefin mixture.

6. The process of claim 1 in which the oligomerized olefins are subsequently hydrogenated.

7. A process for oligomerizing mono olefins comprising contacting
   a. a mixture of alpha olefins which consists essentially of
      (1) greater than 50 weight percent of at least one low molecular weight alpha olefin which is 1-butene and
      (2) less than 50 weight percent of at least one higher molecular weight alpha olefin having 8 to 18 carbon atoms, with
   b. 0.75 to 3.0 weight percent of a catalyst comprising boron trifluoride in the presence of
   c. an organic, protonic promoter selected from the group consisting of alcohols and carboxylic acids, the molar ratio of organic promoter to olefin mixture is from 0.005 to 0.2, at a temperature in the range of about 25° to 75° C. and a pressure that is sufficient to maintain a liquid phase reaction.

8. The process of claim 7 in which the organic, protonic promoter is 1-butanol.

9. The process of claim 7 in which less than 50 weight percent of an inert organic solvent is employed, based on the olefin mixture.

10. The process of claim 1 in which the oligomerized olefins are subsequently hydrogenated.

11. A process for the production of a synthetic lubricant component comprising
    a. oligomerizing a mixture of alpha mono olefins consisting essentially of 1-butene and at least one higher molecular weight alpha olefin having 8 to 18 carbon atoms, where the weight ratio of 1-butene to the higher molecular weight alpha olefins ranges from greater than 1:1 to 3:1, by contacting the mixture with boron trifluoride in the presence of an organic, protonic promoter selected from the group consisting of alcohols and carboxylic acids, at a temperature in the range of about 25° to 75° C. and a pressure that is sufficient to maintain a liquid phase reaction to produce a crude oligomer product,
    b. neutralizing the crude oligomer product,
    c. removing the organic layer from the neutralized crude oligomer product,
    d. hydrogenating the oligomers in the removed organic layer, and
    e. stripping off the molecules having less than 20 carbon atoms, the balance being the synthetic lubricant component.

12. The process of claim 11 in which the catalyst is present in an amount of from 0.75 to 3.0 weight percent, based on the olefin mixture.

13. The process of claim 11 in which the molar ratio of organic, protonic promoter to the olefin mixture is from 0.005 to 0.2.

14. The process of claim 11 in which the protonic promoter is 1-butanol.

15. The process of claim 11 in which less than 50 weight percent of an inert organic solvent is employed, based on the olefin mixture.

16. A synthetic lubricant component having a kinematic viscosity at 210° F. of between 3.0 and 6.0 centistokes being produced by oligomerizing a mixture of alpha mono olefins which consists essentially of 1-butene and at least one higher molecular weight alpha olefin having 8 to 18 carbon atoms, where the weight ratio of 1-butene to the higher molecular weight alpha olefins ranges from greater than 1:1 to 3:1, by means of contacting the alpha olefins with boron trifluoride in the presence of an organic, protonic promoter selected from the group consisting of alcohols and carboxylic acids, at a temperature in the range of about 25° to 75° C. and a pressure that is sufficient to maintain a liquid phase reaction and subsequently hydrogenating the oligomerized olefins.

17. The synthetic lubricant component of claim 16 in which the catalyst is present in an amount of from 0.75 to 3.0 weight percent, based on the olefin mixture.

18. The synthetic lubricant component of claim 16 in which the molar ratio of organic, protonic promoter to the olefin mixture is from 0.005 to 0.2.

19. The synthetic lubricant component of claim 16 in which the protonic promoter is 1-butanol.

20. The synthetic lubricant component of claim 16 in which less than 50 weight percent of an inert organic solvent is present during oligomerization, based on the olefin mixture.

* * * * *